United States Patent
de Looz et al.

(10) Patent No.: US 11,942,237 B2
(45) Date of Patent: Mar. 26, 2024

(54) SYSTEM FOR WIRELINE CABLE COATING

(71) Applicant: Schlumberger Technology Corporation, Sugar Land, TX (US)

(72) Inventors: Marc-Andre de Looz, Sugar Land, TX (US); Bendang Aomeren Imchen, Pune (IN); Vassilis Varveropoulos, Katy, TX (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 720 days.

(21) Appl. No.: 16/792,337

(22) Filed: Feb. 17, 2020

(65) Prior Publication Data

US 2020/0265974 A1 Aug. 20, 2020

Related U.S. Application Data

(60) Provisional application No. 62/806,286, filed on Feb. 15, 2019.

(51) Int. Cl.
| | |
|---|---|
| H01B 13/32 | (2006.01) |
| H01B 7/04 | (2006.01) |
| H01B 13/00 | (2006.01) |
| H02G 1/06 | (2006.01) |

(Continued)

(52) U.S. Cl.
CPC .......... H01B 13/328 (2013.01); H01B 7/046 (2013.01); H01B 13/0003 (2013.01); H02G 1/06 (2013.01);
(Continued)

(58) Field of Classification Search
CPC .............. H01B 13/0003; H01B 13/323; H01B 13/328; H01B 7/046; H02G 1/02;
(Continued)

(56) References Cited

U.S. PATENT DOCUMENTS

| 4,441,113 A | * | 4/1984 | Madan ............... C23C 16/50 |
|---|---|---|---|
| | | | 136/258 |
| 5,331,714 A | | 7/1994 | Essex |

(Continued)

FOREIGN PATENT DOCUMENTS

| CN | 1053179 A | 7/1991 |
|---|---|---|
| CN | 1571643 A | 1/2005 |

(Continued)

OTHER PUBLICATIONS

Erickson et al, "Application of package-level high-performance EMI shield material with a novel nozzleless spray coating technology," 2020 IEEE 70th Electronic Components and Technology Conference (ECTC), 2020, pp. 1691-1696. (Year: 2020).*

(Continued)

*Primary Examiner* — A. Dexter Tugbang
(74) *Attorney, Agent, or Firm* — Ashley E. Brown

(57) ABSTRACT

A cable coater system for a downhole tool includes a cable coater. The cable coater may include a housing and one or more rollers that are coupled to the housing, wherein the one or more rollers are configured to rest on the downhole cable while guiding the cable through openings in the cable coater during wireline operations. The cable coater may remain on cable during all spooling (on and off) activities for the duration of operations and activated to coat the cable upon the final pull out of hole and prior to storage of the cable. The spooling in and out of the cable may further be automatically controlled by providing a positional indicator of the cable coater and thus where the cable is in three-dimensional space relative the spool.

8 Claims, 6 Drawing Sheets

(51) Int. Cl.
  *C23C 16/50*     (2006.01)
  *H02G 1/02*      (2006.01)
  *H02G 11/02*     (2006.01)

(52) U.S. Cl.
  CPC .......... *C07C 2521/02* (2013.01); *C23C 16/50* (2013.01); *H01B 13/323* (2013.01); *H02G 1/02* (2013.01); *H02G 11/02* (2013.01)

(58) Field of Classification Search
  CPC ...... H02G 11/02; H02G 1/06; C07C 2521/02; C23C 16/50; C09D 7/40
  See application file for complete search history.

(56) References Cited

U.S. PATENT DOCUMENTS

2009/0054713 A1* 2/2009 Matkovsky ......... C07C 2521/02
                                                  585/326
2014/0010954 A1* 1/2014 Hobson, III ............. H02G 1/02
                                                  348/125
2017/0110220 A1* 4/2017 Romer .................. H02G 11/02

FOREIGN PATENT DOCUMENTS

| | | |
|---|---|---|
| CN | 1768663 A | 5/2006 |
| CN | 108821037 A | 11/2018 |
| EP | 2221647 A2 | 8/2010 |
| FR | 2768849 A1 | 3/1999 |
| JP | 2008525568 A | 7/2008 |
| JP | 2017091633 A * | 5/2017 |

OTHER PUBLICATIONS

CN First Office Action; Application No. 202010096195X; dated Dec. 28, 2023; 13 pages with English Translation.

* cited by examiner

SYSTEM FOR WIRELINE CABLE COATING

CROSS-REFERENCE TO RELATED APPLICATIONS

This disclosure claims the benefit of and priority to U.S. Provisional Patent Application No. 62/806,286, titled "System and Method for Cable Coating," filed Feb. 15, 2019, which is incorporated by reference herein in its entirety for all purposes.

BACKGROUND

This disclosure relates generally to downhole tools and more specifically to tools for coating wireline cables for downhole tools.

This section is intended to introduce the reader to various aspects of art that may be related to the present techniques, which are described and/or claimed below. This discussion is believed to be helpful in providing the reader with background information to facilitate a better understanding of the present disclosure. Accordingly, it should be understood that these statements are to be read in this light, and not as admissions of prior art.

A wellbore drilled into a geological formation may be targeted to produce oil and/or gas from only certain zones of the geological formation. After or during certain wellbore operations, it is desirable to get more information about the formation in the wellbore using wireline cable. Wireline cables may accumulate debris and wellbore fluids as they are used within the wellbore, which may result in damage of cables due to degradation of the armor and/or jackets of the cable. A cable coater or cleaner may be employed to clean the cables or coat them with liquids such as inhibitors and/or grease. Certain conventional cable coaters may add additional stress to the cables, which may result in damage of the cables.

SUMMARY

A summary of certain embodiments disclosed herein is set forth below. These aspects are presented merely to provide the reader with a brief summary of these certain embodiments and that these aspects are not intended to limit the scope of this disclosure. Indeed, this disclosure may encompass a variety of aspects that may not be set forth below.

One embodiment of the present disclosure relates to a cable coater system for a downhole tool including a cable coater. The cable coater may include a housing having a recess, a first opening, and a second opening that are configured to receive a downhole cable. In some embodiments, the cable coater may include one or more nozzles disposed on the housing, wherein the one or more nozzles configured to direct a flow of liquid onto the downhole cable disposed in the recess. Further, the cable coater may include one or more rollers that are coupled to the housing, wherein the one or more rollers are configured to guide the downhole cable through the first opening, the recess, and the second opening. In addition, the cable coater may include fiducials on any number of exterior surfaces, allowing the coater itself to aid in visual processing and automation of the spooling process. The fiducials can include but are not limited to, circles, ovals, polygons, lines and crossed lines of any number. In some embodiments, the cable coater may apply a lubricant that may change the optical properties (e.g., reflection, color, spectrum in a particular wavelength range, and so forth) such that application of the lubricant may be detected. In some embodiments, the lubricant may include a dopant that may impart a larger change in optical properties. In any case, detection of the downhole cable may allow for positional tracking of the downhole cable based at least in part on certain predetermined, known, and/or input information relating to properties of the cable and/or storage of the cable (e.g., when the cable is stored on a spool or drum) such as cable thickness, diameter of spool, time of run, and so forth. Positional tracking of the downhole cable may be based on fiducials located on the cable coater itself, optical properties of the cable, or combinations thereof.

Various refinements of the features noted above may be undertaken in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which.

DETAILED DESCRIPTION

Figure 1:
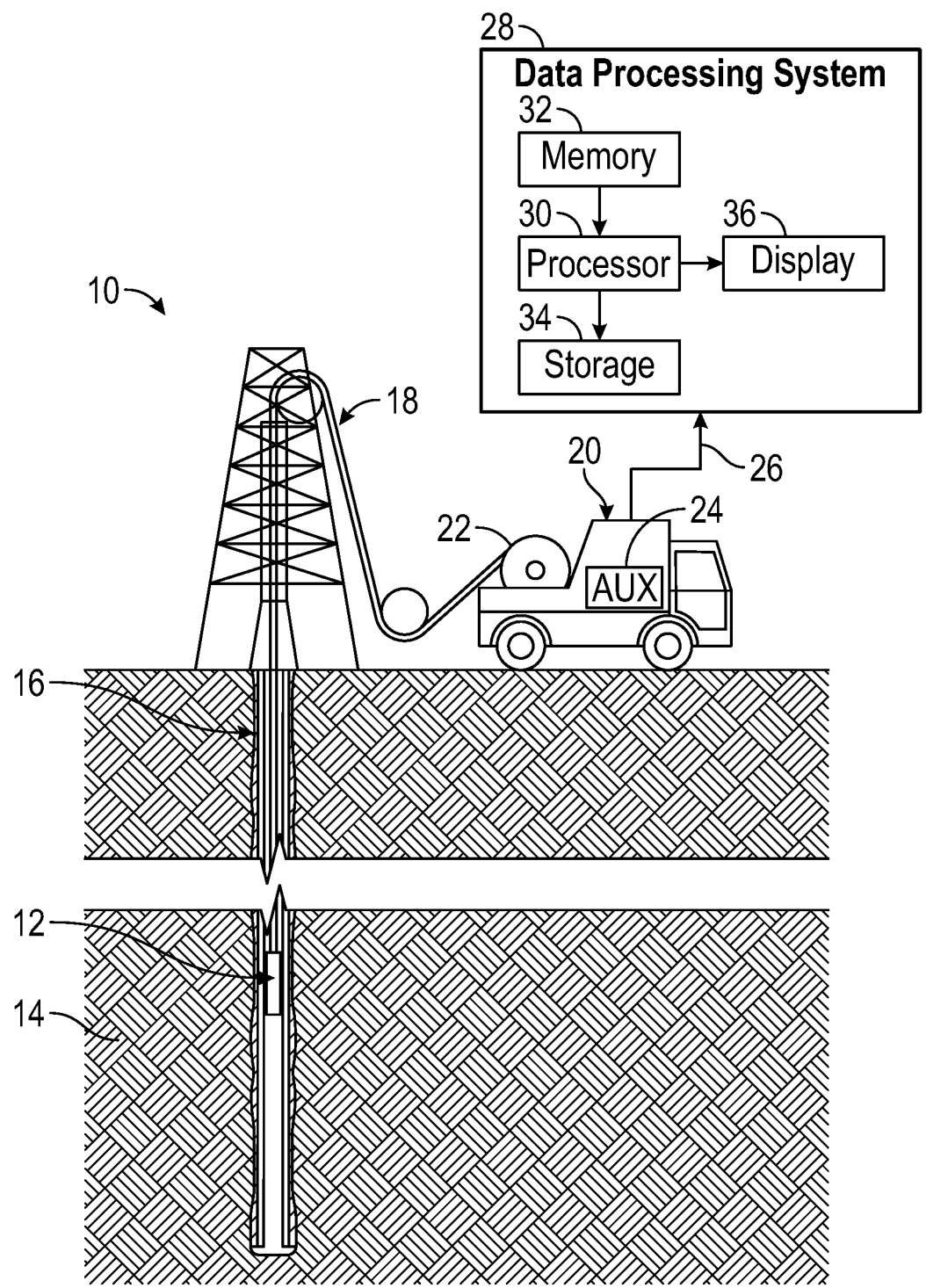
FIG. 1 is a partial cross sectional view of a well-logging and perforating system that may be used to bring a well into production, perform well diagnostics, or remediate or repair a well after it has been drilled through the subsurface formations, in accordance with an embodiment of the present techniques.

One or more specific embodiments of the present disclosure will be described below. These described embodiments are only examples of the presently disclosed techniques. Additionally, to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, references to "one embodiment" or "an embodiment" of the present disclosure are not intended to be interpreted as excluding the existence of additional embodiments that also incorporate the recited features.

Wireline cables accumulate debris and wellbore fluids as they are used in-hole. The debris and wellbore fluids, if uncleaned can result in damage to cables through degradation of the armor or jackets. Cable cleaners are used in wireline operations to clean the cable as it is pulled out of hole (POOH), and a cable coater can be used to coat the cable with inhibitors, grease, or other fluids depending on the specific need. A roller-suspended coater presented below is used to coat the cable. Spooling of the cable may be fully automatable through intelligent connection to a wireline truck or a substantially fixed installation, which is configurable to have and monitor information such as cable diameter, logging speed/winch speed and where in the run the spooling is. The automatic control of the cable spooling can increase the efficiency of the complete job and may further be used in conjunction with cable cleaners and coaters.

The present disclosure relates to a wireline cable coater system (e.g., cable coater system) that prevents damage that may occur during storage and/or in subsequent use. In conventional cable coater systems, cables could be damaged during operation (i.e., running in and out of hole) due to friction with the cable coater during operation. As such, conventional cable coater systems need to be removed during run-in-hole (RIH) and POOH operations. Adding a roller to a cable coater system and, in certain embodiments, adjustable features such as flanges and/or spacers may reduce the frictional force applied to the cable as it moves through the cable coater, and thus reduce, the likelihood of damage applied to the cable when running in or out of hole. Therefore, the cable coater may be left on the cable during the entire operation, which may reduce man-hours associated with maintenance and removal of such devices in addition to reducing the likelihood of damaging the cable when running in and out of hole. Many steps in spooling the cable may be automated. In some embodiments, the coater may operate as part of either partially or completely automated spooling through the intelligent connection to the wireline truck or fixed installation, which can determine positional information of the cable based at least in part on the cable diameter, logging speed (e.g., winch speed) and where in the run the spooling is. The automatic control of spooling the cable in and out of hole as well as coating the cable on the last spooling (final) will increase the efficiency of the complete job.

With this in mind, FIG. 1 illustrates a well-logging system 10 that may employ the systems and methods of this disclosure. The well-logging system 10 may be used to convey a downhole tool 12 through a geological formation 14 via a wellbore 16. The downhole tool 12 may be conveyed on a cable 18 via a logging winch system 20. Although the logging winch system 20 is schematically shown in FIG. 1 as a mobile logging winch system carried by a truck, the logging winch system 20 may be substantially fixed (e.g., a long-term installation that is substantially permanent or modular). Any suitable cable 18 for well logging may be used. The cable 18 may be spooled and unspooled on a drum or spool 22 and an auxiliary power source 24 may provide energy to the logging winch system 20 and/or the downhole tool 12.

Moreover, although the downhole tool 12 is described as a wireline downhole tool, it should be appreciated that any suitable conveyance may be used. For example, the downhole tool 12 may instead be conveyed as a logging-while-drilling (LWD) tool as part of a bottom hole assembly (BHA) of a drill string, conveyed on a slickline or via coiled tubing, and so forth. For the purposes of this disclosure, the downhole tool 12 may be any suitable measurement tool that obtains logging measurements through depths of the wellbore 16. For example, such logging measurements may include, but are not limited to, density, resistivity, photoelectric absorption properties, neutron spectroscopy, and the like.

To this end, the data processing system 28 thus may be any electronic data processing system that can be used to carry out the systems and methods of this disclosure. For example, the data processing system 28 may include a processor 30, which may execute instructions stored in memory 32 and/or storage 34. As such, the memory 32 and/or the storage 34 of the data processing system 28 may be any suitable article of manufacture that can store the instructions. The memory 32 and/or the storage 34 may be ROM memory, random-access memory (RAM), flash memory, an optical storage medium, or a hard disk drive, to name a few non-limiting examples. A display 36, which may be any suitable electronic display, may provide a visualization, a well log, or other indication of properties in the geological formation 14 or the wellbore 16 using logging measurements 26.

Figure 2:
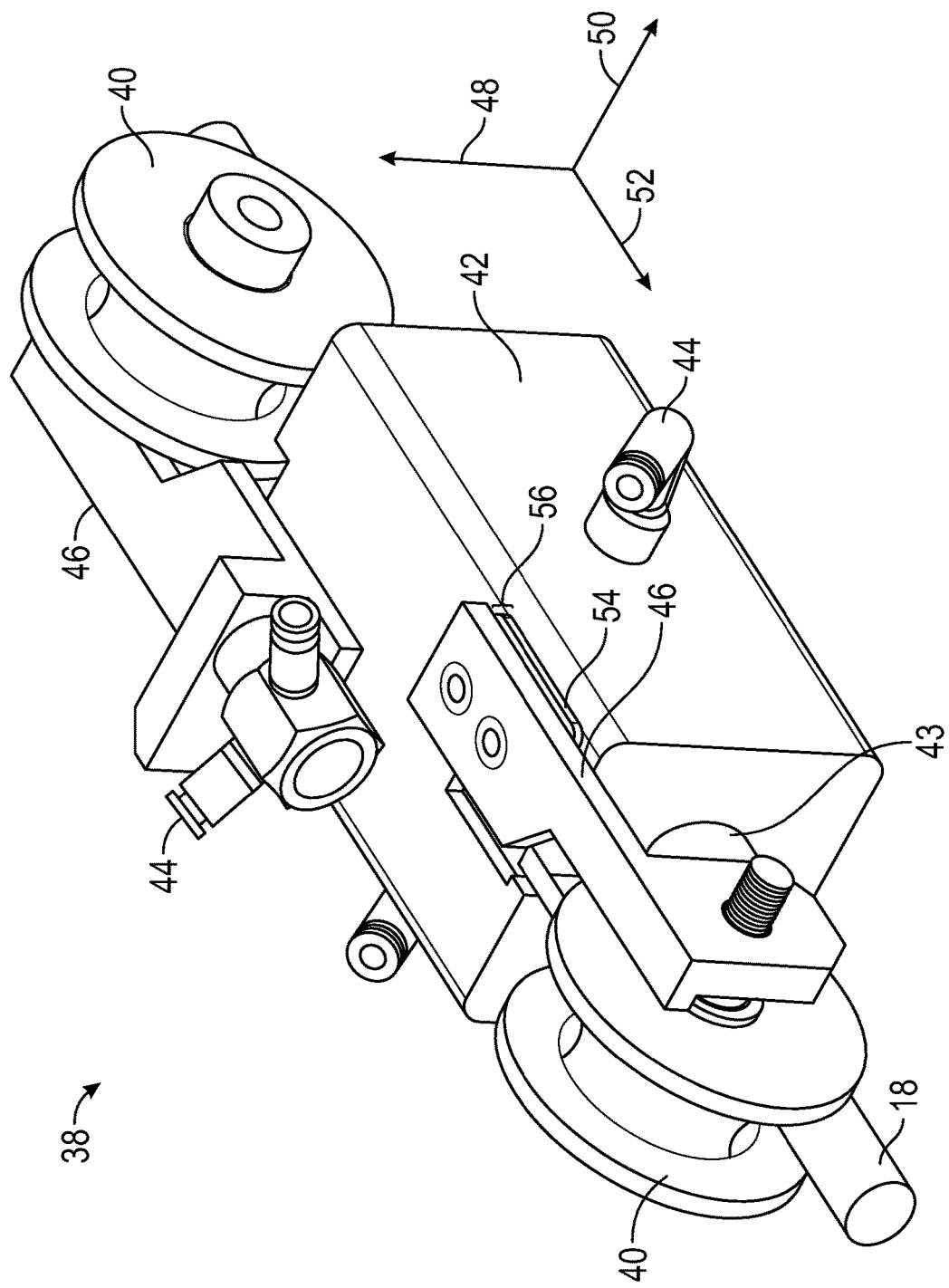
FIG. 2 is a schematic diagram of a cable coater with rollers, in accordance with an embodiment of the present techniques.

The addition of centralizing rollers on the cable coater will transfer the load point to the rollers as opposed to bushings typically installed at cable entry and exit points of conventional cable coating devices. As the rollers rotate, there is no reactionary force (friction) applied to the cable inhibiting milking damage, which may allow for continuous use. An additional advantage of this design is the ability to run the cable in and out of hole. That is, the cable coater can be installed at the beginning of the job and removed at the end. It should be appreciated that this may reduce excess time of labor associated with set up of the cable coater during downhole operations. Because the cable coater may be deployed throughout the job, the cable coater may further be used as part of a system to automatically control the cable spooling. FIG. 2 is a schematic diagram of a cable coater 38 with rollers 40 in accordance with aspects of the present disclosure. The illustrated embodiment of the cable coater 38 shown in FIG. 2 also includes a housing 42 where fluid, such as a type of lubricant, may be applied to the cable 18. The housing 42 includes a recess or channel, a first opening 43, and a second opening 47 that are configured to receive a downhole cable. Additionally, the cable coater 38 includes one or more nozzles 44 disposed on the housing 42 of the cable coater than may receive and direct a flow of fluid to the cable that is within the housing 42. As illustrated, the housing 42 is generally box-shaped or cuboid, but it should be appreciated that in some embodiments the housing 42 may be any shape including, but not limited to, ovoid, cylindrical, spherical, and cubical.

As illustrated, the cable coater 38 may include one or more flanges 46 that couple the rollers 40 to the housing 42 of the cable coater 38. The flanges 46 may have a suitable shape such that the rollers 40 receive the cable 18 at a suitable height (e.g., along the axis 48), lateral position (e.g., along axis 50), and/or distance from the housing (e.g., along axis 52) to space the cable 18 in a position to pass through the first opening 43, recess, and second opening 47. Keeping the cable positioned and generally aligned with the first and second openings 43, 47 along axes 48, 50, where a central axis of the cable is aligned or closely aligned and/or overlapping with a central axis of the first opening, recess, and second opening, reduces friction and/or milking of the cable to improve longevity of the cable 18. In addition, the flanges 46 may have a suitable shape to also accommodate different shaped housings as described above. In some embodiments, one or more spacers 54 may be disposed between the flanges 46 and the housing 42. The spacers 54 may have a suitable shape and thickness 56 such that the roller 40 is offset along the axis 48 to fit cables of different thicknesses. As such, at least one of the rollers 40 and the flange 46 may remain constant during operations when different cables 18 of different thicknesses are used. Put differently, it may be easier to replace on the spacer 54, while using the same roller 40 and/or flange 46. As illustrated, only one spacer 54 is used per flange 46, but it should be appreciated that in some embodiments multiple spacers 54 may be used per flange 46 to position the rollers 40 and/or flange 46 at a suitable height (e.g., along axis 48) along the housing 42.

Figure 3:
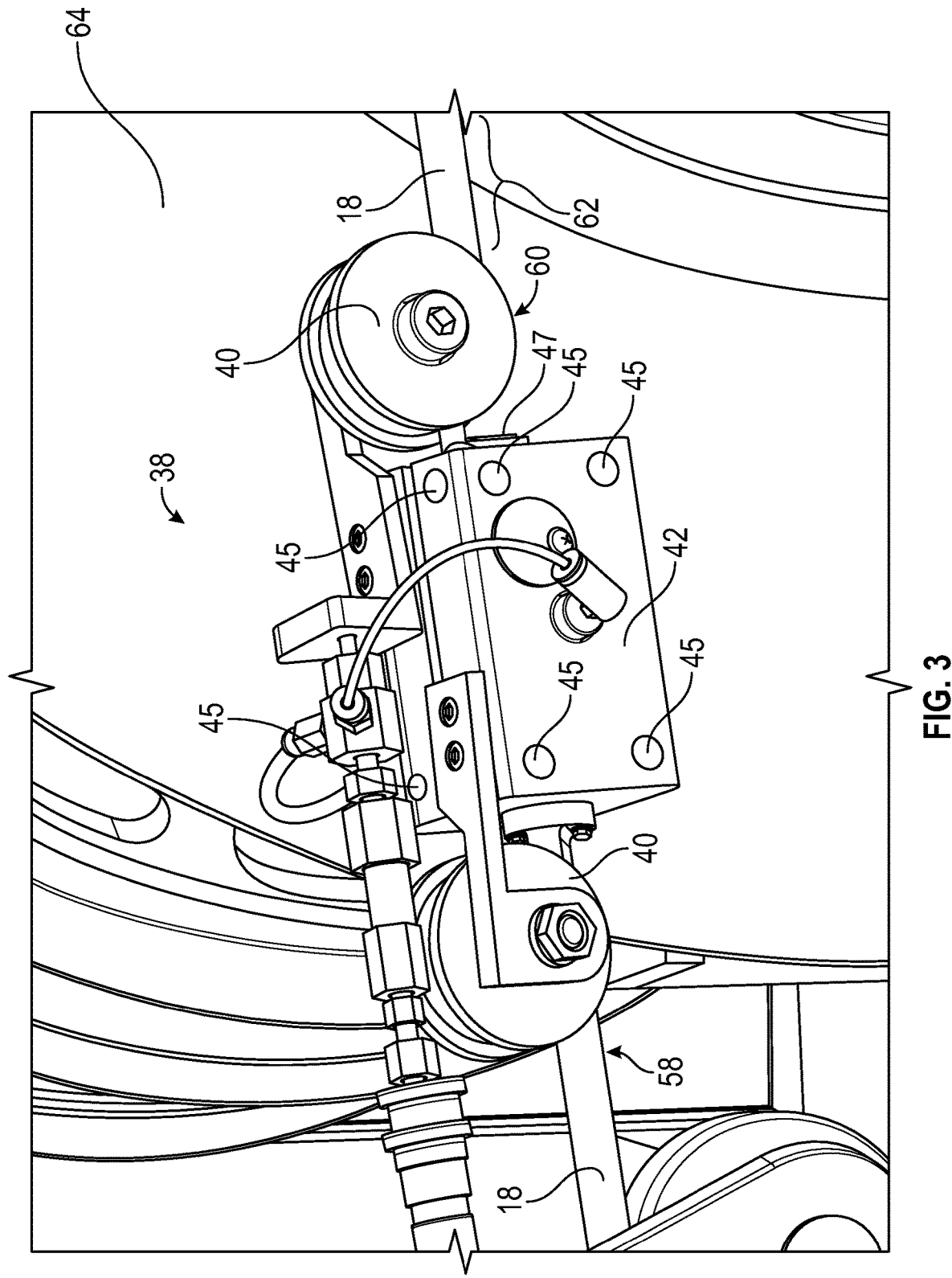
FIG. 3 is an image of a cable coater with a cable from a first perspective, in accordance with an embodiment of the present techniques.

FIG. 3 is an image of a cable coater 38 in operation proximate a spool 64, in accordance with aspects of the present disclosure. As discussed herein, the cable coater 38 may receive a cable 18 via the rollers 40. For example, the cable 18 may be directed from a downstream position 58 to an upstream position 60. However, it should be appreciated that, in some embodiments, the cable 18 may be directed in the reverse direction (e.g., from the upstream position 60 to the downstream position 58). In any case, the cable 18 directed toward the upstream position may receive a fluid (e.g., a lubricant, or lubricant having a dopant) while the cable 18 passes through the housing 42. The dopant may be a solid or liquid that may change the optical properties visible at the surface of the cable 18. For example, cable 18 within and/or after the region 62 may have a different optical property such as color, reflectivity, and/or an optical signal at a non-visible region of light (e.g., near- or mid-infrared, ultraviolet, and so forth). In another embodiment, the lubricant may be sufficient for producing a change in the optical properties of the cable 18 (e.g., able to be detected by a detector such as a camera). As such, the change in optical property at the surface of the cable 18 is indicative of successful coating of the cable 18 with the lubricant by the cable coater 38.

Another aspect of the present disclosure is directed to a positional locator of the cable. That is, the cable coater 38 can be used as a position or location indicator of where the cable is in three-dimensional space. The housing 42 of the cable coater 38 may further include fiducials 45 disposed at predetermined and known locations. The fiducials 45 may be any shape recognizable by a detector known in the art including, but not limited to, circles, ovals, polygons, lines, and crossed lines of any number. As the cable coater 38 is positioned on the cable 18 and proximate the spool 64, shape of the cable coater 38 itself or the fiducials 45 can be used to positionally located the cable coater 38 and thus the cable 18 as it passes through the cable coater 38. This allows visual automation algorithms used to automatically control spooling to have a much higher accuracy and decreased error over the course of the wireline job; the cable coater shape itself and the fiducials can be used as easily recognizable positional locators (data points) for processing. For example, visual automation algorithms may receive data indicative of the position of the cable via position of the cable coater 38 and/or the fiducials 45 relative the spool 64.

Figure 4:
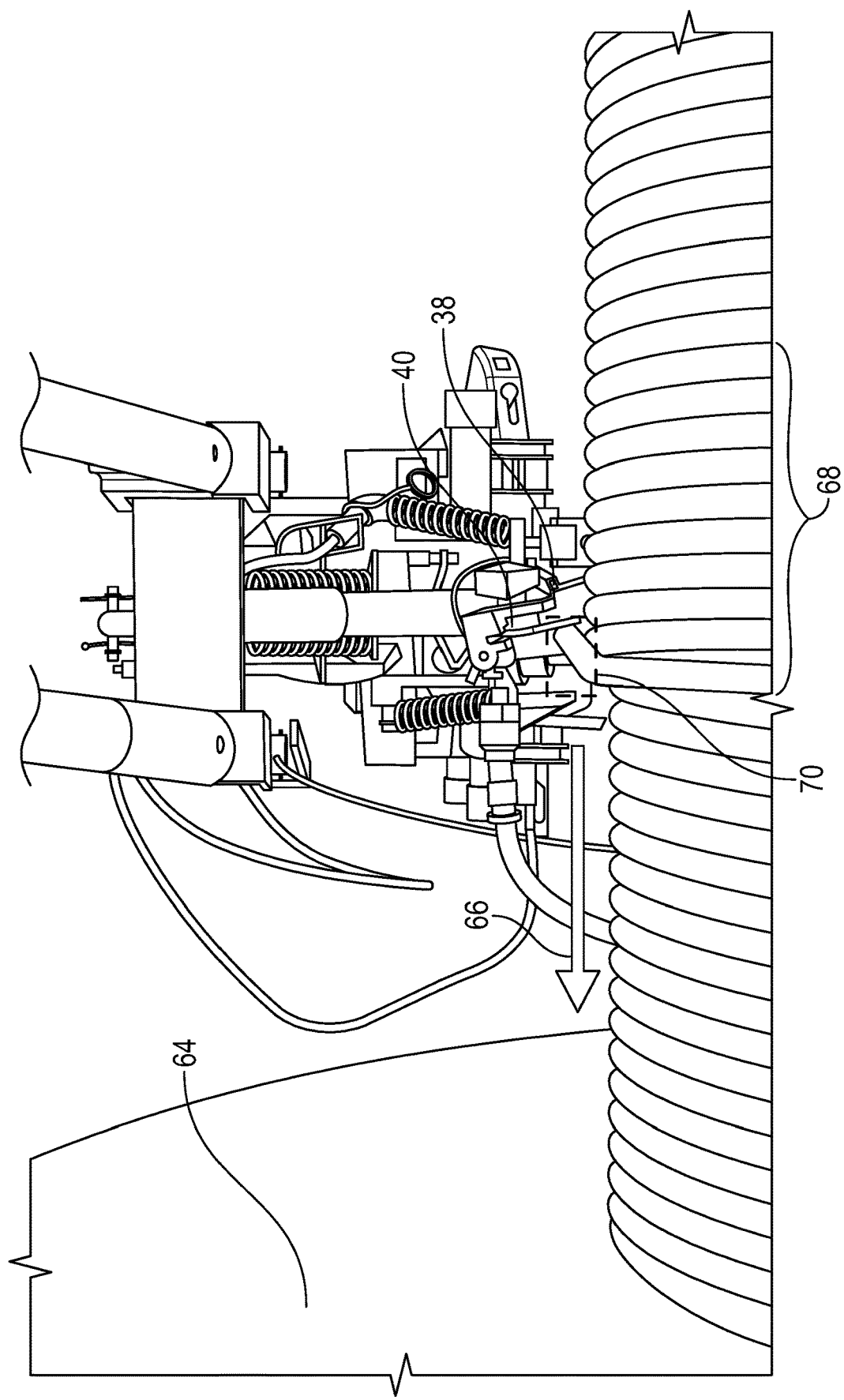
FIG. 4 is an image of a cable coater from a second perspective, in accordance with an embodiment of the present techniques.

FIG. 4 is an additional image of the cable coater 38 from a second perspective, in accordance with aspects of the present disclosure. In particular, FIG. 4 shows cable coater 38 disposed on cable 18 being positioned on a spool 64. In this embodiment, the cable 18 is being added along the direction 66. Additionally, the cable 18 along region 68 may have different optical properties than the rest of the cable on the spool 66 as the optical property may be less apparent as the lubricant dries or settles, or is obstructed by subsequently added cable 18. In any case, it is presently recognized that the optical properties of the cable 18 leaving the cable coater 38 may facilitate tracking of the cable.

In some embodiments, the cable 18 within region 70 may be used for positional tracking of the cable 18. For example, an angle of the cable 18 within the region 70 from the roller 40 may be used to determine positional information of the cable 18. As it should be appreciated, the angle may also be determined relative to other points on the image such as a center point, or the angle between the cable 18 within the region 70 and the cable in the region 68. Alternatively, position of the cable may also be determined using a linear distance (e.g., in the direction 66) and/or how much cable 18 has been added to the spool 64 based on time information and/or reflectivity measurements. Further, visual automation algorithms may use data indicative of the angle, linear distance, time, reflectivity measurements, or combinations thereof to automatically control spooling.

Figure 5:
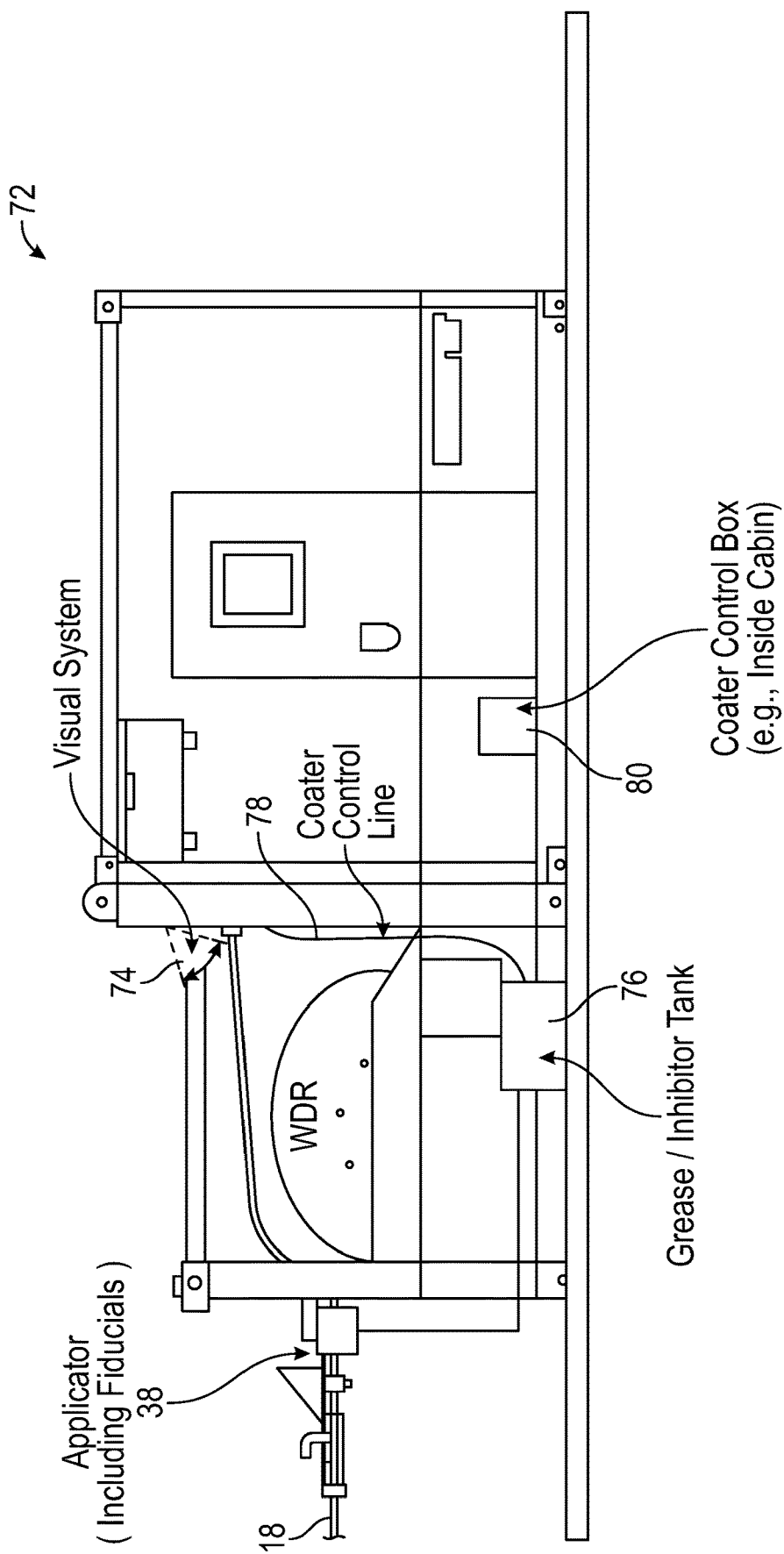
FIG. 5 is a side view of a cable coater, in accordance with an embodiment of the present techniques.

FIG. 5 is a schematic diagram of cable coater system 72 for tracking a position of the cable 18, in accordance with aspects of the present disclosure. As shown in the illustrated embodiment of the cable coater system 70 of FIG. 3, the cable coater system 72 includes the cable coater 38, a detector 74, a grease or inhibitor tank 76, a coater control line 78, and a coater control box 80. In some embodiments, the coater control box 80 may be the data processing system 28. In any case, the cable coater 38, detector 74, grease or inhibitor tank 76, coater control line 78, and coater control box 80 generally cooperate to facilitate position tracking of the cable 18 by applying lubricant to the cable 18, detecting a change in optical property of the cable 18 due to the added lubricant or a dopant within the lubricant, and determining positional information of the cable based on the change, or lack of change, of the optical property. In some embodiments, predetermined information relating to the geometry or size of the cable may be used in such a determination as discussed herein.

Figure 6:
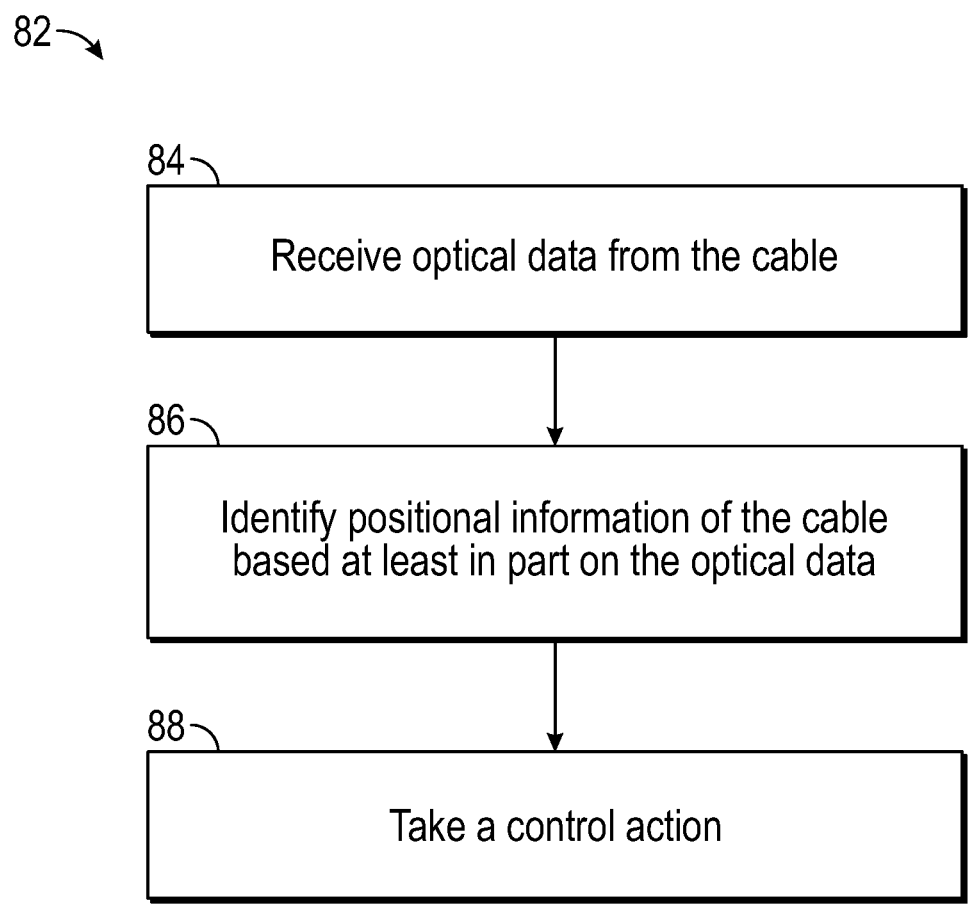
FIG. 6 is a flow diagram for taking control actions relating to the operation of the cable based at least in part on optical data related to the cable, in accordance with an embodiment of the present techniques.

FIG. 6 is a flow diagram 82 for tracking a position of a cable 18, in accordance with aspects of the present disclosure. In general, the flow diagram 82 may include receiving optical data indicative of the position of a cable coater to provide feedback to a data processing system or operator. The elements illustrated in the flow diagram 82 may be performed by the data processing system 28 or any suitable processing system.

The illustrated embodiment of the flow diagram 82 in FIG. 6 begins with receiving (e.g., block 84) optical data. For example, this may include receiving a picture, or taking a video and extracting pixels with a signal above or below a threshold that is indicative of the shape of the cable coater 38 itself, fiducials 45, or a presence and/or absence of a lubricant and/or dopant within the lubricant. The flow diagram also includes identifying (e.g., block 86) a position of the cable. As discussed herein, this may be based on predetermined, known information relating to the cable, the optical data, and/or input from, for example, an operator with information about the cable. Additionally, the flow diagram 82 includes taking (e.g., block 88) control action, which may be automated. For example, control action may include sending suitable control signals to halt retraction of the cable or direct the spooling control arm of the cable.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A cable coater system for a downhole tool, the system comprising:
   a cable coater comprising:
      a housing having a recess, a first opening, and a second opening that are configured to receive a downhole cable; and
      one or more nozzles disposed on the housing, wherein the one or more nozzles are configured to direct a flow of liquid onto the downhole cable disposed in the recess;
   one or more rollers coupled to the housing;
      wherein the one or more rollers are configured to guide the downhole cable through the first opening, the recess, and the second opening; and
   one or more fiducials disposed on the housing configured to be used to positionally locate the downhole cable.

2. The cable coater system of claim 1, further comprising a detector configured to measure a property of the liquid disposed on the cable.

3. The cable coater system of claim 2, wherein the property of the liquid is a property of a dopant within the liquid.

4. The cable coater system of claim 2, further comprising a control system configured to:
   determine positional information of the downhole cable based at least in part on the measured property of the liquid; and
   perform a control action based on the measured property.

5. The cable coater system of claim 1, further comprising one or more flanges disposed between the rollers and the housing.

6. The cable coater system of claim 5, wherein the one or more flanges is configured to position and align the downhole cable with the first and second openings.

7. The cable coater system of claim 1, further comprising one or more spacers disposed between the rollers and the housing.

8. The cable coater system of claim 7, wherein the one or more spacers is disposed between the one or more flanges and the housing.

* * * * *